(12) United States Patent
Lindner (10) Patent No.: US 8,273,126 B2
(45) Date of Patent: Sep. 25, 2012

(54) VERTEBRAL BODY REPLACEMENT IMPLANT AND INSTRUMENT FOR HANDLING THE VERTEBRAL BODY REPLACEMENT IMPLANT

(75) Inventor: Stephan Lindner, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 688 days.

(21) Appl. No.: 12/321,762

(22) Filed: Jan. 22, 2009

(65) Prior Publication Data

US 2009/0192611 A1 Jul. 30, 2009

(30) Foreign Application Priority Data

Jan. 29, 2008 (DE) .......................... 10 2008 006 491

(51) Int. Cl.
*A61F 2/44* (2006.01)
(52) U.S. Cl. ................. 623/17.15; 623/16.11; 623/17.11
(58) Field of Classification Search ................ 623/17.11, 623/16.11, 17.12, 17.15
See application file for complete search history.

(56) References Cited

U.S. PATENT DOCUMENTS

| | | | |
|---|---|---|---|
| 5,989,290 A | 11/1999 | Biedermann et al. | |
| 6,176,881 B1 | 1/2001 | Schär et al. | |
| 6,200,348 B1 | 3/2001 | Biedermann et al. | |
| 6,524,341 B2 | 2/2003 | Lang et al. | |
| 2002/0161441 A1 | 10/2002 | Lang et al. | |
| 2005/0060036 A1 | 3/2005 | Schultz et al. | |
| 2007/0093901 A1 | 4/2007 | Grotz et al. | |

FOREIGN PATENT DOCUMENTS

| | | |
|---|---|---|
| DE | 198 04 765 | 8/1999 |
| DE | 10 2005 022 920 | 11/2006 |
| EP | 1 121 075 | 8/2001 |

*Primary Examiner* — Thomas J Sweet
*Assistant Examiner* — Matthew Schall
(74) *Attorney, Agent, or Firm* — Lipsitz & McAllister, LLC (57) ABSTRACT

In a vertebral body replacement implant having a bottom locating part for positioning against a lower vertebral body and having a top locating part for positioning against an upper vertebral body, wherein both locating parts are telescopically displaceable relative to one another in the manner of a piston-cylinder unit, having a sealed hydraulic chamber formed by the locating parts, having a charging opening leading into the hydraulic chamber for a hydraulic medium, which upon entering the hydraulic chamber pushes the two locating parts apart from one another, and having a locking device, which may be activated by means of an instrument and upon activation fixes the two locating parts non-displaceably relative to one another, in order to facilitate the handling of the vertebral body replacement implant it is proposed that the locking device is disposed on the vertebral body replacement implant in the region of the charging opening. An instrument for handling the vertebral body replacement implant is also proposed.

6 Claims, 10 Drawing Sheets

VERTEBRAL BODY REPLACEMENT IMPLANT AND INSTRUMENT FOR HANDLING THE VERTEBRAL BODY REPLACEMENT IMPLANT

The present disclosure relates to the subject matter disclosed in German patent application 10 2008 006 491.2 of Jan. 29, 2008, which is incorporated herein by reference in its entirety and for all purposes.

BACKGROUND OF THE INVENTION

The invention relates to a vertebral body replacement implant having a bottom locating part for positioning against a lower vertebral body and having a top locating part for positioning against an upper vertebral body, wherein both locating parts are telescopically displaceable relative to one another in the manner of a piston-cylinder unit, having a sealed hydraulic chamber formed by the two locating parts, having a charging opening leading into the hydraulic chamber for a hydraulic medium, which upon entering the hydraulic chamber pushes the two locating parts apart from one another, and having a locking device, which may be activated by means of an instrument and upon activation fixes the two locating parts non-displaceably relative to one another.

Such a vertebral body replacement implant is described for example in US 2005/0060036 A1. This mode of construction makes it possible to adjust the spacing of the two locating parts in accordance with the spacing of the vertebral bodies that come into abutment on either side of the vertebral body replacement implant and then to fix the two locating parts relative to one another in the spacing adjusted by the hydraulic medium. After the fixing the hydraulic medium may be removed, the spacing of the two locating parts then being maintained exclusively by means of the locking device.

In the known vertebral body replacement implant, the charging opening for the hydraulic medium is disposed in the lower part of the one locating part, the fixing device in the upper part, so that in order to introduce the hydraulic medium, on the one hand, and actuate the locking device, on the other hand, a relatively large access is required because the appropriate instruments have to brought alongside one another towards the vertebral body replacement implant.

The object of the invention is to design a vertebral body replacement implant of the above general type in such a way that the handling, i.e. the filling with the hydraulic medium and the locking of the locking device, is possible through as small a body access as possible.

SUMMARY OF THE INVENTION

In a vertebral body replacement implant of the initially described type, this object is achieved according to the invention in that the locking device is disposed on the vertebral body replacement implant in the region of the charging opening. By virtue of the spatial juxtaposition of the charging opening, on the one hand, and the locking device, on the other hand, the appropriate instruments that are needed to introduce hydraulic medium and actuate the locking device may also act substantially in the same region of the vertebral body replacement implant, thereby allowing these instruments to be brought towards the vertebral body replacement implant through a much smaller body access.

It is particularly advantageous if the charging opening and. the locking device are disposed coaxially with one another. In particular, the locking device may surround the charging opening.

In a preferred embodiment it is provided that the charging opening is disposed in a charging connection piece and that the locking device surrounds the charging connection piece.

It is particularly advantageous if the locking device comprises a screw that is screwable into a thread of the one locating part and in the process presses directly or by means of an intermediate element against the other locating part and thereby fixes the other locating part relative to the one locating part.

In particular, the screw may have a central through-channel that surrounds the charging connection piece. In this way, a particularly space-saving arrangement is obtained.

The intermediate element may be a ring that surrounds the charging opening.

A further underlying object of the invention is to provide an instrument for handling the vertebral body replacement implant of the previously described type that allows handling of the implant through as small a body access as possible.

This object is achieved according to the invention by an instrument for handling the vertebral body replacement implant having the features of one of claims 1 to 7, having an elongate shank, on the distal end of which holding elements for the vertebral body replacement implant are disposed, wherein the instrument is characterized in that disposed in the shank are a hydraulic tube, which may be positioned sealingly against the charging opening of the vertebral body replacement implant, and an actuating element, which passes through the shank and which upon positioning of the shank against the vertebral body replacement implant moves into working connection with the locking device.

In this way, a single instrument, in which all of the active elements are surrounded by an elongate shank, may be used to handle the vertebral body replacement implant as well as both to fill the vertebral body replacement implant with the hydraulic medium and to actuate the locking device.

The hydraulic tube and a charging connection piece of the vertebral body replacement implant that accommodates the charging opening may in particular be configured to be plugged in a sealed manner one into the other.

In this case, it is advantageous if the hydraulic tube and the charging connection piece in the region of their plug-in connection are of a rotationally symmetrical design so that they can be twisted relative to one another about a common longitudinal axis while maintaining the sealing effect.

In a particularly preferred embodiment, it is provided that the hydraulic tube additionally performs the function of the actuating element for the locking device, so that the hydraulic tube and the actuating element are one and the same component. This is advantageous particularly if the hydraulic tube is plugged together with the charging connection piece in a rotatable manner, thereby allowing the rotational movement of the hydraulic tube to be used to actuate the locking device.

In this case, it may be provided that the hydraulic tube and the locking device upon positioning of the shank against the vertebral body replacement implant form a positive rotational connection, so that a rotation of the hydraulic tube about its longitudinal axis leads to a twisting of the locking device about the same axis of rotation.

According to a further advantageous development, it may be provided that there is disposed in the shank a clamping apparatus, which when actuated clamps the shank in a position against the vertebral body replacement implant, in which the hydraulic tube is positioned in a sealing manner against the charging opening. In this case, it is advantageous if the clamping apparatus comprises a pull member, which is disposed between hydraulic tube and shank and on the distal end of which at least one gripping projection is disposed, which engages behind a clamping projection on the locating part accommodating the charging opening and upon displacement of the pull member in proximal direction clamps the locating part against the shank.

In a preferred embodiment it is provided that gripping projections are disposed at diametrically opposite sides of the pull member, that the gripping projections are held on arms that are flexibly bendable radially apart from one another and that the radially outwardly bendable arms are movable by displacement of the shank relative to the pull member between a deployment position, in which the arms project from the shank and are therefore bendable radially apart from one another, and a clamping position, in which the shank overlaps the arms and prevents the arms from bending radially apart from one another. It is therefore easily possible to bring the gripping projections into abutment behind the clamping projections, it being sufficient for this purpose to shift the pull member into the deployment position, in which the gripping projections may be bent radially apart from one another to such an extent that the clamping projections slide through between them. By retracting the pull member, the arms that are flexibly bendable apart from one another are pushed into the shank, which then prevents the arms from bending apart from one another, so that the gripping projections have to remain in their position of engagement behind the clamping projections.

The gripping projection or gripping projections may preferably have a convexly curved locating face, and it is also advantageous if the clamping projections have a concavely curved locating face.

It is particularly advantageous if the pull member takes the form of a sleeve that surrounds the hydraulic tube and fills the gap between the hydraulic tube, on the one hand, and the shank, on the other hand.

The shank on its distal end may carry extensions, which project in distal direction and which upon abutment of the shank with the vertebral body replacement implant engage into corresponding receiving indentations of the vertebral body replacement implant. These projections therefore position the vertebral body replacement implant relative to the shank, so that the clamping apparatus just clamps the shank and the vertebral body replacement implant against one another, while the relative alignment of the shank to the vertebral body replacement implant is guaranteed substantially by means of the extensions that engage into the receiving indentations.

On the proximal end of the shank a handle may be disposed, which is preferably designed to be detachable from the shank.

It is advantageous if the hydraulic tube at its proximal end projects from the shank and carries gripping faces there for twisting the hydraulic tube about its longitudinal axis.

It may further be provided that the pull member on its proximal end carries an actuating device, upon the actuation of which the pull member in the shank is displaceable relative thereto in longitudinal direction.

This actuating device may for example comprise a turning element, which may be screwed onto the pull member and which is supported against the shank. By twisting the turning element, the turning element is screwed to a greater or lesser extent onto the pull member and therefore displaces the pull member relative to the shank.

The following description of preferred embodiments of the invention is used in connection with the drawings to provide a detailed explanation.

DETAILED DESCRIPTION OF THE INVENTION

In the drawings a vertebral body replacement implant is represented, that is referred to hereinafter merely as implant 1. This implant 1 may be handled with the aid of a handling instrument 2, which may be detachably connected to the implant 1.

First, there now follows a detailed description of the structure of the implant 1 with reference to FIGS. 3 to 9.

Figure 1:
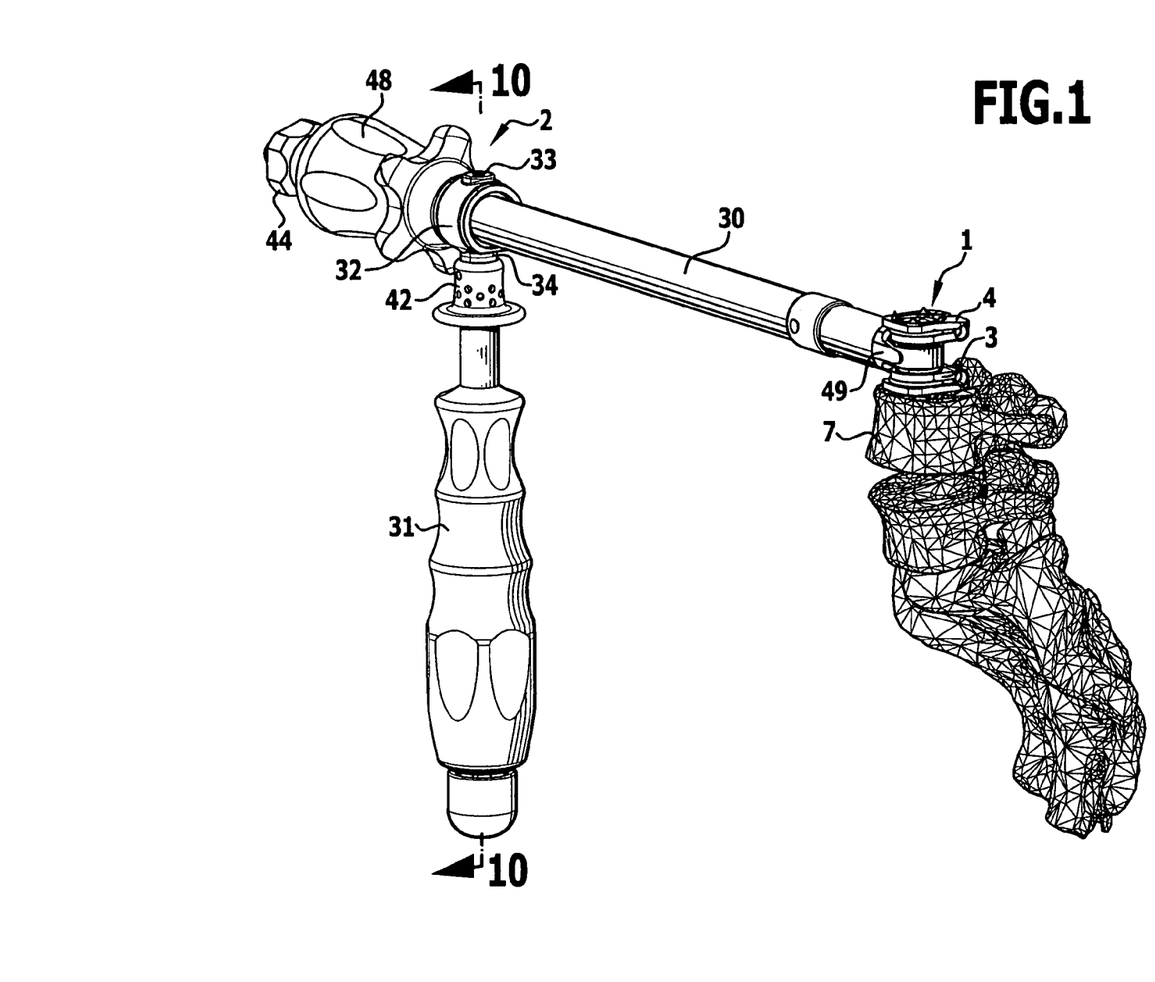
FIG. 1: is a perspective view of a handling apparatus for a vertebral body replacement implant with a vertebral body replacement implant tightly clamped thereon during positioning of the vertebral body replacement implant in the spinal column.
Figure 2:
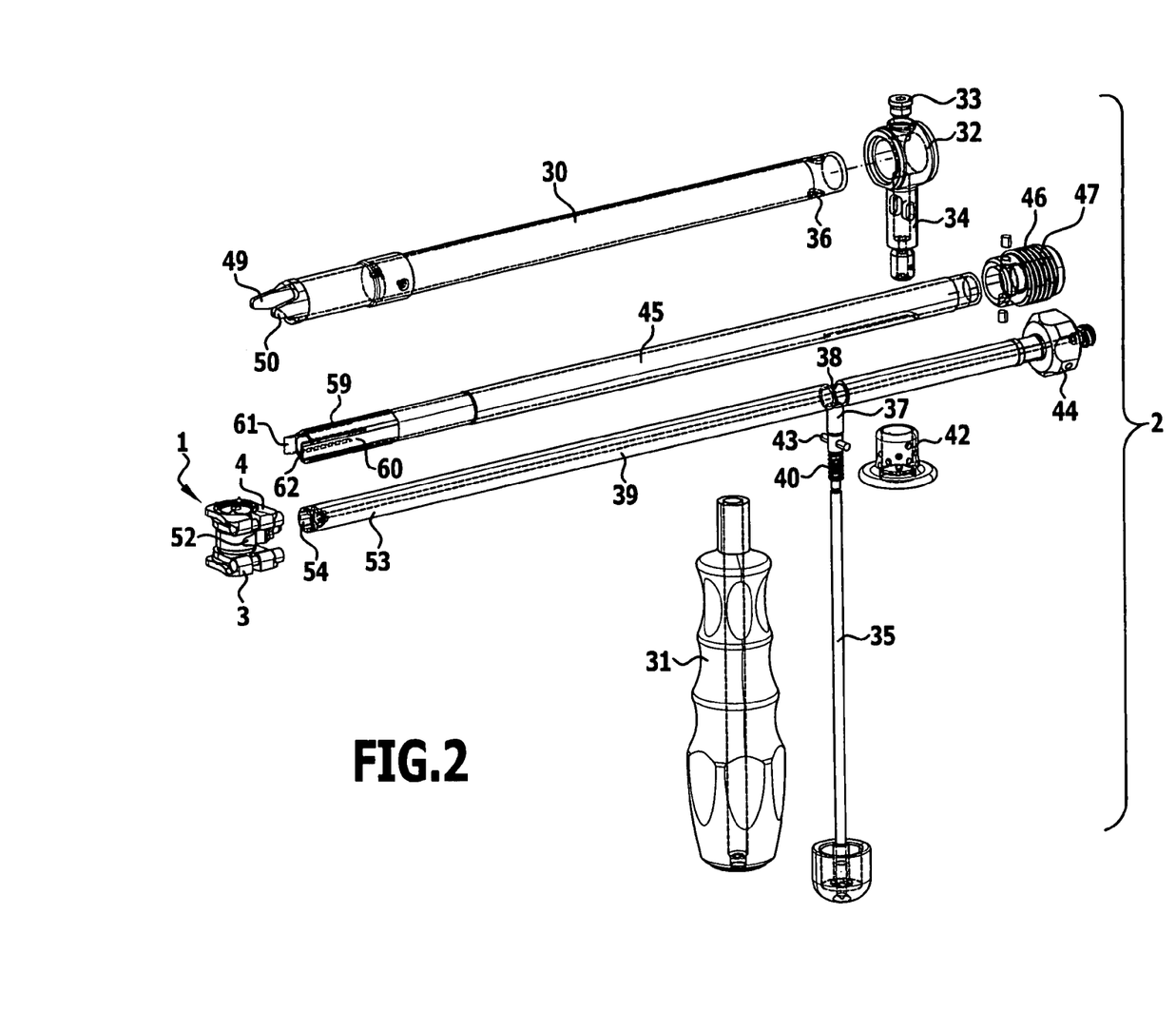
FIG. 2: is an exploded view of the handling instrument of FIG. 1 with the various individual parts of the handling instrument and a vertebral body replacement implant.
Figure 3:
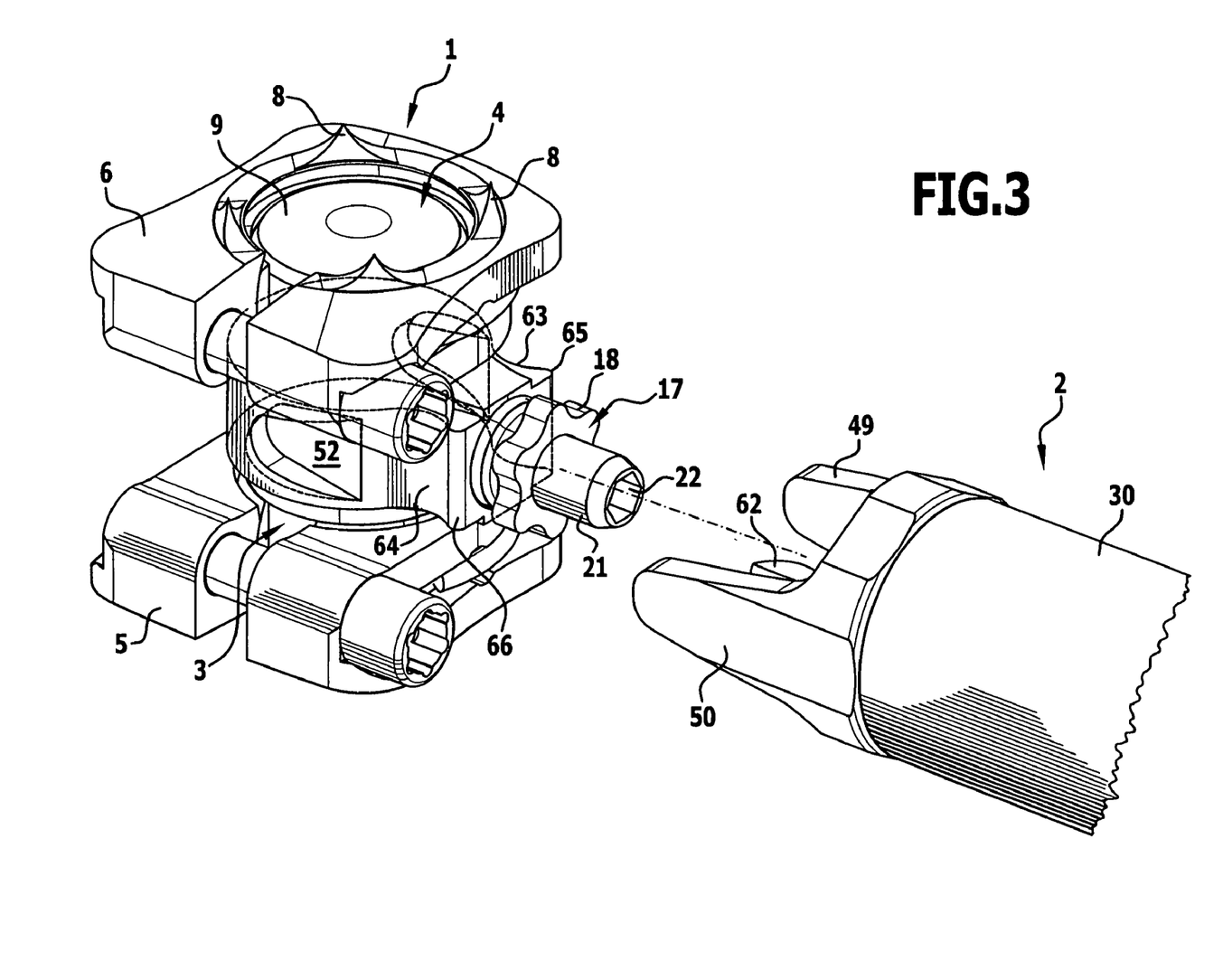
FIG. 3: is a perspective view of a vertebral body replacement implant prior to placing on the distal end of a handling instrument.

The implant comprises a bottom locating part 3 and a top locating part 4, each of locating parts 3 and 4 carrying an annular support plate 5 and/or 6, the mutually remote end faces of which form locating faces, by which the implant 1, which is to replace a vertebral body, may be positioned against adjacent vertebral bodies. This is evident from the illustration of FIG. 1, in which however only the vertebral body 7 lying adjacent to the bottom locating part 3 is shown. The support plates 5, 6 carry pointed projections 8, which are oriented in each case in the direction of the adjacent vertebral bodies and which when positioned against the adjacent vertebral bodies penetrate into these and hence secure the locating faces of the support plates 5, 6 against a lateral displacement relative to the vertebral bodies.

The top locating part 4. has substantially the shape of a circular cylinder that is closed at its top end 9 and open at its bottom end 10. The bottom locating part 3 likewise has a circular-cylindrical shape and is closed at its bottom end 11 and open at its top end 12. The bottom end 11 in this case is of a relatively thick construction, the outside diameter at the upper end of the bottom end 11 decreasing in a stepped manner, so that the upper portion 13 of the bottom locating part 3 has an outside diameter that corresponds to the inside diameter of the cylindrical top locating part 4. The portion 13 engages into the top locating part 4 and is freely displaceable in longitudinal direction relative thereto, so that the bottom locating part 3 and the top locating part 4 are slidable telescopically apart from and towards one another.

Figure 4:
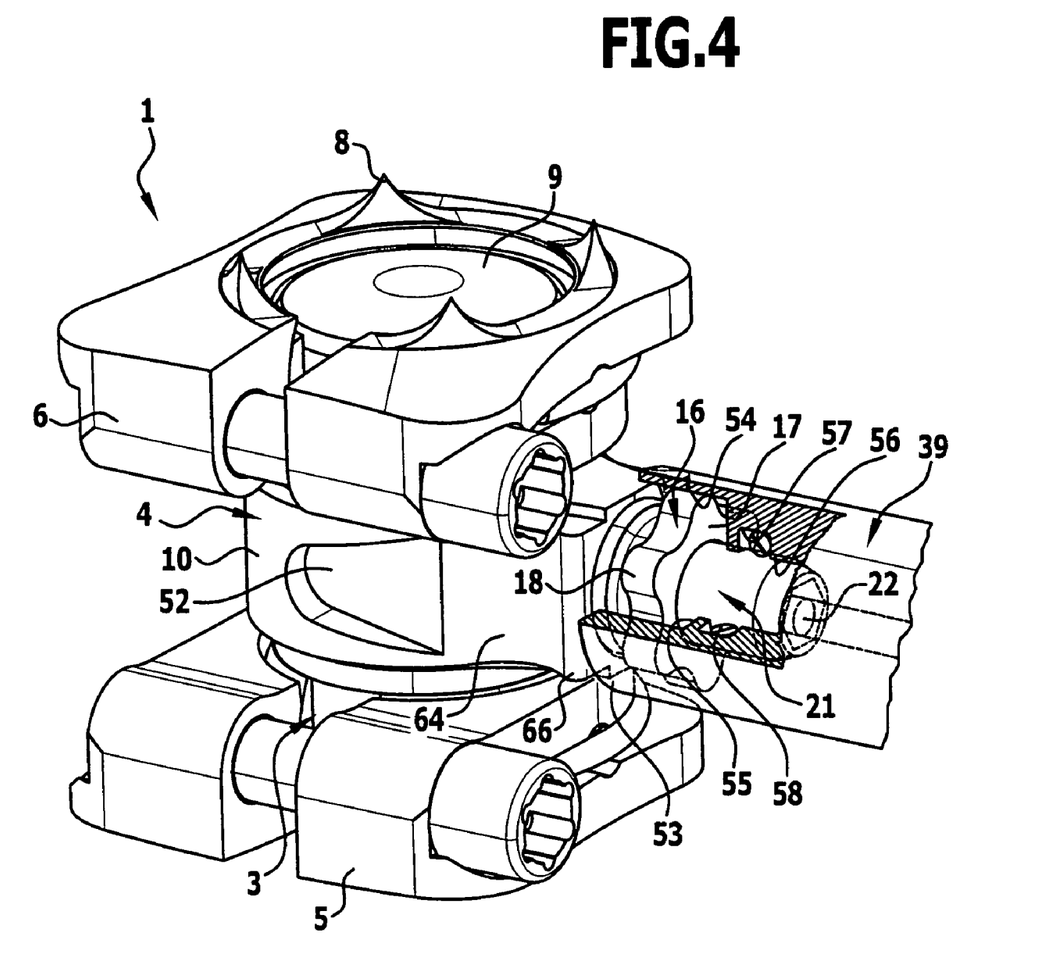
FIG. 4: is a perspective view of the vertebral body replacement implant, onto which has been placed a hydraulic tube that is represented partially cut open.
Figure 5:
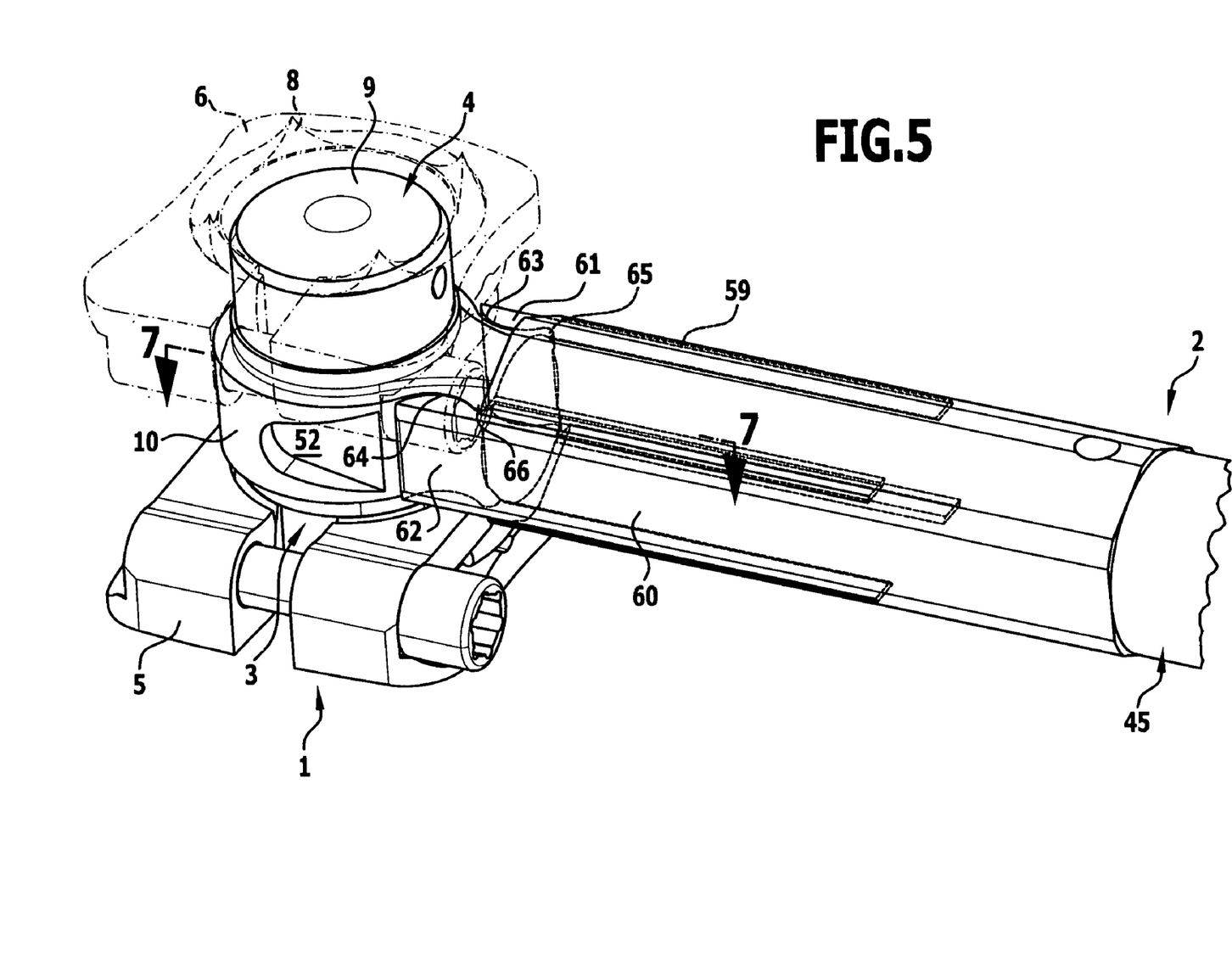
FIG. 5: is a perspective view of the vertebral body replacement implant with hydraulic tube and pull member placed thereon, but without representation of the shank.
Figure 6:
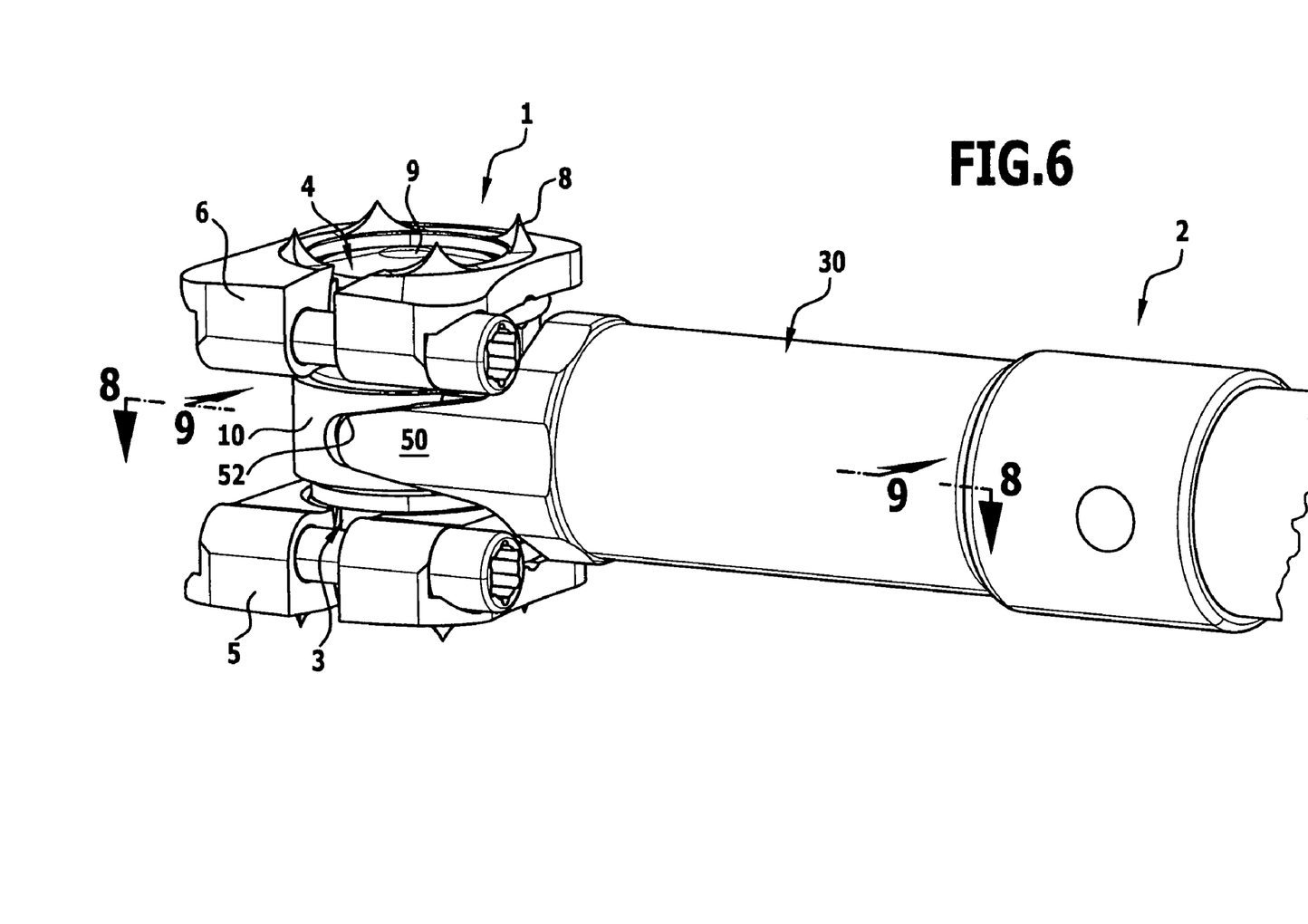
FIG. 6: is a perspective view of the vertebral body replacement implant with a handling instrument placed thereon.

Moulded onto the top locating part 4 adjacent to its bottom end 10 is a radially projecting, internally threaded connection piece 14, into which an attachment screw 16 having a central through-channel 15 is screwed. Outside of the internally threaded connection piece 14 this attachment screw 16 carries a widened head 17 having a non-circular cross section, the head in the illustrated embodiment carrying radially protruding projections 18 that are arc-shaped in cross section, the overall result therefore being a rosette-shaped cross section (FIG. 4).

Inserted in the interior of the cylindrical portion 13 of the bottom locating part 3 is a tubular piece 19, which is closed at the bottom and open in an upward direction and which at its bottom end has a lateral opening 20, which is aligned with the internally threaded connection piece 14 and into which is screwed a charging connection piece 21, which passes through the channel 15 of the attachment screw 16. The charging connection piece 21 lies against the inner wall of the channel 15, and a flow channel 22 that passes through the charging connection piece 21 is in communication with the interior 23 of the tubular piece 19.

The charging connection piece 21 passes through the side wall of the portion 13 of the bottom locating part 3 in an elongate hole 24 that extends over a large part of the height of the portion 13. This elongate hole 24 is surrounded by a indentation 25 in the outer wall of the portion 13, the base 26 of which is substantially perpendicular to the longitudinal axis of the charging connection piece 21. Engaging into this indentation 25 is a clamping ring 27, which is mounted so as to surround the charging connection piece 21 and be longitudinally displaceable thereon and against which the attachment screw 16 is supported. When the attachment screw 16 is screwed into the internally threaded connection piece 14, the clamping ring 27 is pressed towards the base 26 of the indentation 25 and therefore fixes the portion 13 relative to the charging connection piece 21 and hence relative to the top locating part 4 in the relative position occupied in each case.

The tubular piece 19 is surrounded above the top end 12 of the portion 13 by an annular seal 28 that seals off the interior of the top locating part 4 from the tubular piece 19. This interior is in communication with the interior of the tubular piece 19 and with the flow channel 22 of the charging connection piece 21. When a hydraulic medium, for example a physiological saline, is introduced through the flow channel 22 into this interior and when it is introduced under pressure, the result is that the interior increases in size, i.e. the top locating part 4 and the bottom locating part 3 are pushed telescopically apart from one another, i.e. the spacing between the two support plates 5 and 6 is increased. The top locating part 4 therefore forms the cylinder and the bottom locating part 3 the piston of a structure corresponding to that of a hydraulically actuable piston-cylinder unit.

The adjustment of the mutual spacing of the two support plates 5 and 6 is therefore effected by filling the interior to a greater or lesser extent with a hydraulic medium, the fixing of the spacing once achieved then being effected by tightening the attachment screw 16 and hence pressing the clamping ring 27 towards the base 26 of the indentation 25. Once a fixing has been effected in this manner, the interior may be emptied, i.e. the hydraulic medium may be removed, the spacing of the two support plates 5 and 6 then being maintained.

Given the described design of the implant 1, it is important that the attachment screw 16 is disposed coaxially with the charging connection piece 21 so that the filling of the interior with the hydraulic medium and the actuation of the attachment screw 16 may be effected along a common axis. In order to be able to carry out these actions, the handling instruments 2 is of an appropriate design.

The handling instrument 2 comprises an elongate, tubular shank 30 that is connected at its proximal end detachably to a handle 31 that projects radially from the shank 30. For this purpose, the handle 31 by means of an annular holding eyelet 32 disposed on its upper end surrounds the shank 30, a fastening screw 33 being screwed in radial direction into this holding eyelet 32 and fastening the holding eye 32 to the shank 30 in the screwed-in state. Immediately adjacent to the holding eyelet 32 a holding journal 34 is moulded thereon, this holding journal 34 projecting into the handle 31, which is connected detachably to the holding journal 34 by means of a holding rod 35, which fully passes through the handle 31 and may be screwed into the holding journal 34.

Mounted in a longitudinally displaceable manner in the interior of the holding journal 34 is a retaining pin 37, which projects through a hole 36 in the shank 30 and engages into a circumferential groove 38 of a charging tube 39, which is disposed in the interior of the shank 30 and fully passes through the shank 30. Supported against the retaining pin 37 is a helical spring 40, the other end of which rests against a step 41 in the interior of the holding journal 34, this helical spring 40 pressing the retaining pin 37 into the circumferential groove 38. Thus, the charging tube 39 is mounted in the shank 30 so as to be non-displaceable in longitudinal direction and at the same time freely twistable about the longitudinal axis.

The holding journal 34 is surrounded by a gripping sleeve 42, which is mounted in a longitudinally displaceable manner on the holding journal 34 and which is connected by a transverse pin 43 to the retaining pin 37, so that the gripping sleeve 42 and the retaining pin 37 move jointly along the holding journal 34. By means of the gripping sleeve 42 the retaining pin 37 may be displaced counter to the action of the helical spring 40, with the result that the retaining pin 37 moves out of the circumferential groove 38 and enables a free longitudinal displacement of the charging tube 39 in the shank 30.

The charging tube 39 projects from the shank 30 at the proximal end thereof and carries a turning handle 44 there, with the aid of which the charging tube 339 may be twisted about its longitudinal axis. The interior of the charging tube 39 at its proximal end may be connected in a manner not evident from the drawing to a source for a hydraulic medium, for example to a syringe body, by means of which a physiological saline may be passed through the charging tube 39.

The charging tube 39 is directly surrounded by a clamping sleeve 45, which fills the gap between the charging tube 39 on the one hand and the shank 30 and which in the region between the proximal end of the shank 30 and the turning handle 44 of the charging tube 39 is connected in a rotationally fixed manner to a stopper 46, which is mounted in a longitudinally displaceable manner on the charging tube 39. The clamping sleeve 45 is accommodated in the shank 30 so as to be non-rotatable about the longitudinal axis, so that the stopper 46 too is mounted in a non-rotatable but longitudinally displaceable manner on the charging tube 39. The stopper 46 carries an external thread 47, onto which is screwed a turning handle 48, which coaxially surrounds the charging tube 39 and is supported at its distal end against the holding eyelet 32. When the turning handle 48 is rotated, the turning handle 48 is screwed onto the external thread 47 and therefore draws the clamping sleeve 45 in proximal direction into the shank 30.

On the distal end the shank 30 carries two diametrically opposite projections 49, 50, which protrude in distal direction and fit into two mutually opposite, lateral indentations 51, 52 in the outer wall of the top locating part 4, these indentations 51 and 52 being situated at the level of the charging connection piece 21 and the attachment screw 16 surrounding this charging connection piece 21. When the projections 49 and 50 are introduced into the indentations 51 and 52, the projections 49 and 50 are applied laterally against the base of the indentations 51 and 52 and moreover against the lateral edges of the indentations 51 and 52, thereby achieving a defined orientation of the implant 1 relative to the shank 30 when the shank 30 is pressed in distal direction towards the implant 1.

The distal end 53 of the charging tube 39 has a recess 54, which is open towards the distal end and the cross section of which corresponds to the cross section of the head 17 of the attachment screw 16, i.e. in the illustrated embodiment has the shape of a rosette. This recess 54 passes over via a step 55 into a proximally adjoining central sealing aperture 56, the inside diameter of which corresponds to the outside diameter of the charging connection piece 21. In the side wall of the sealing aperture 56 there is disposed in a circumferential groove 57 an annular seal 58, which is applied sealingly against the outside of the charging connection piece 21 when the charging tube 39 is advanced in distal direction towards the implant 1 and at the same time the charging connection piece 21 enters the sealing aperture 56.

In this way, a sealed connection is established between the flow channel 22 of the charging connection piece 21, on the one hand, and the interior of the charging tube 39, on the other hand.

The clamping sleeve 45 on two mutually opposite sides of its distal end carries two arms 59, 60, which project in distal direction and each carry on their distal end a radially inwardly projecting gripping projection 61 and 62 respectively. These gripping projections 61 and 62 and the associated arms 59 and 60 are disposed directly alongside the distal projections 49 and 50 of the shank 30 and engage into lateral recesses 63, 64 on the top locating part 4 that adjoin the indentations 51 and 52 in proximal direction. The proximal ends of the recesses 63 and 64 form radially outwardly protruding clamping projections 65 and 66.

The gripping projections 61 and 62 are designed to be convexly curved in cross section, and in a corresponding manner the recesses 63 and 64 are designed to be concavely curved in cross section, so that the gripping projections 61 and 62 may engage into the recesses 63 and 64 in such a way that the recesses 63 and 64 are substantially filled by the gripping projections 61 and 62.

Figure 7:
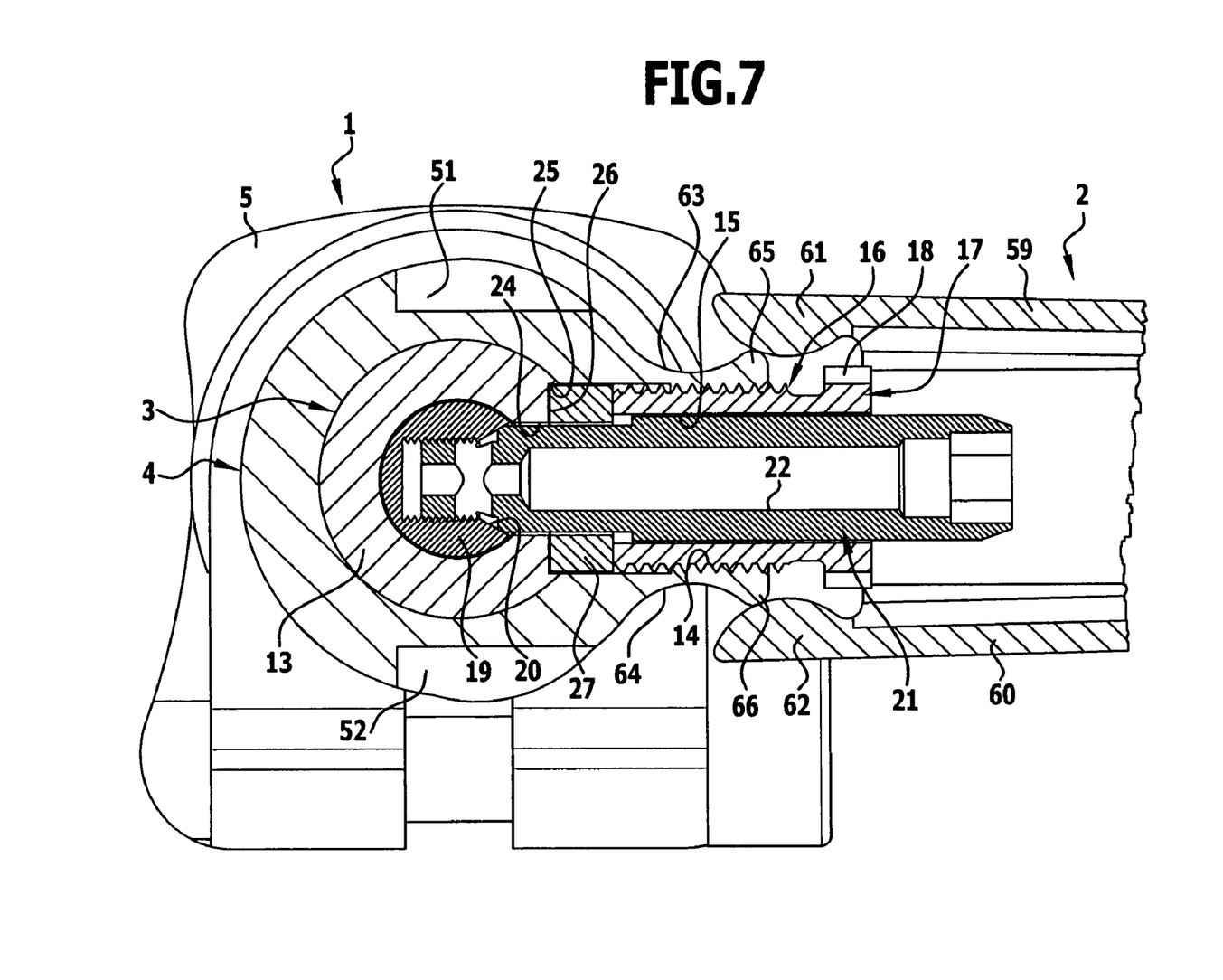
FIG. 7: is a sectional view of the vertebral body replacement implant and the pull member along line 7-7 in FIG. 5.
Figure 8:
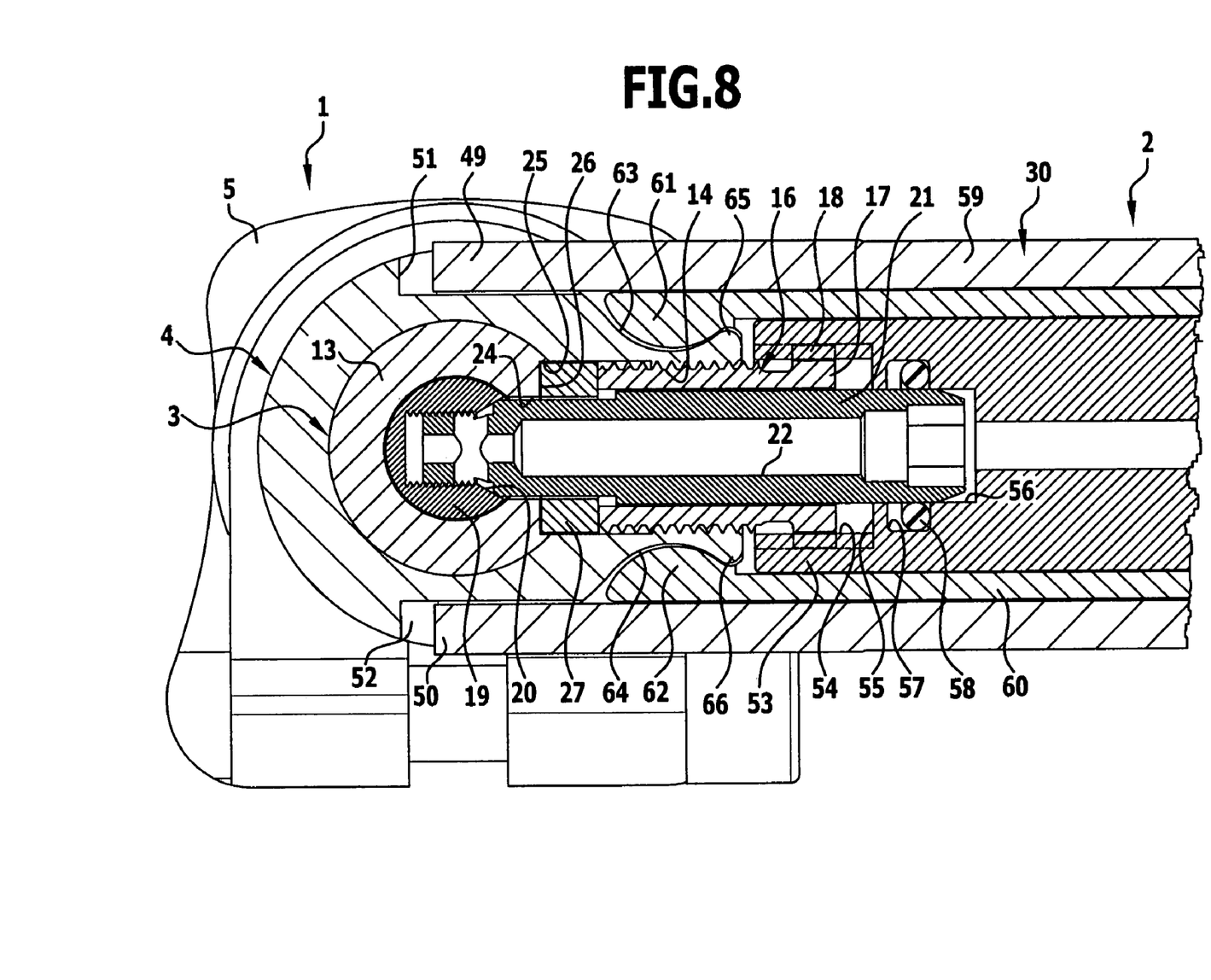
FIG. 8: is a sectional view along 8-8 in FIG. 6.
Figure 9:
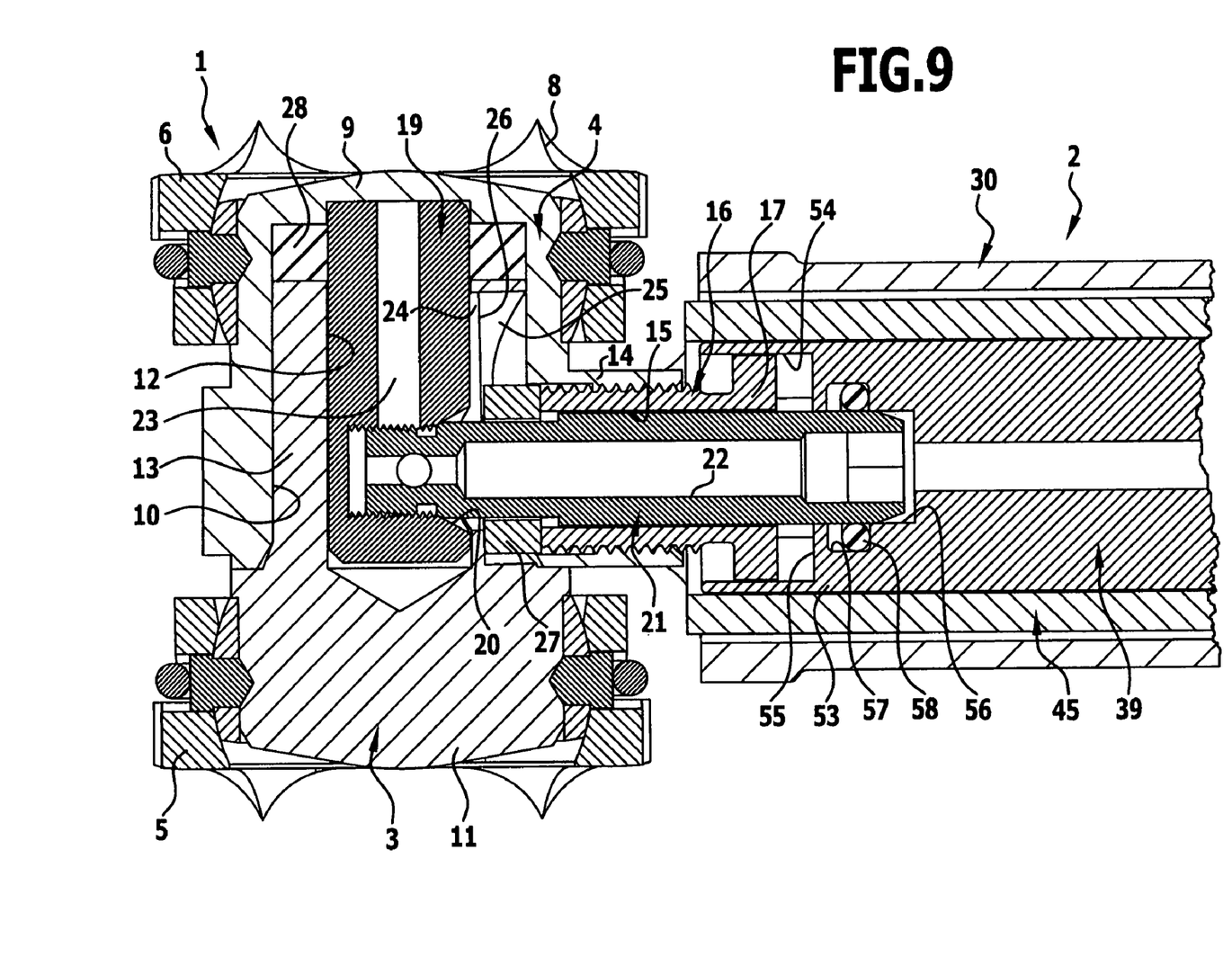
FIG. 9: is a sectional view along line 9-9 in FIG. 6 and FIG. 10: is a sectional view of the proximal part of the handling instrument along line 10-10 in FIG. 1.
Figure 10:
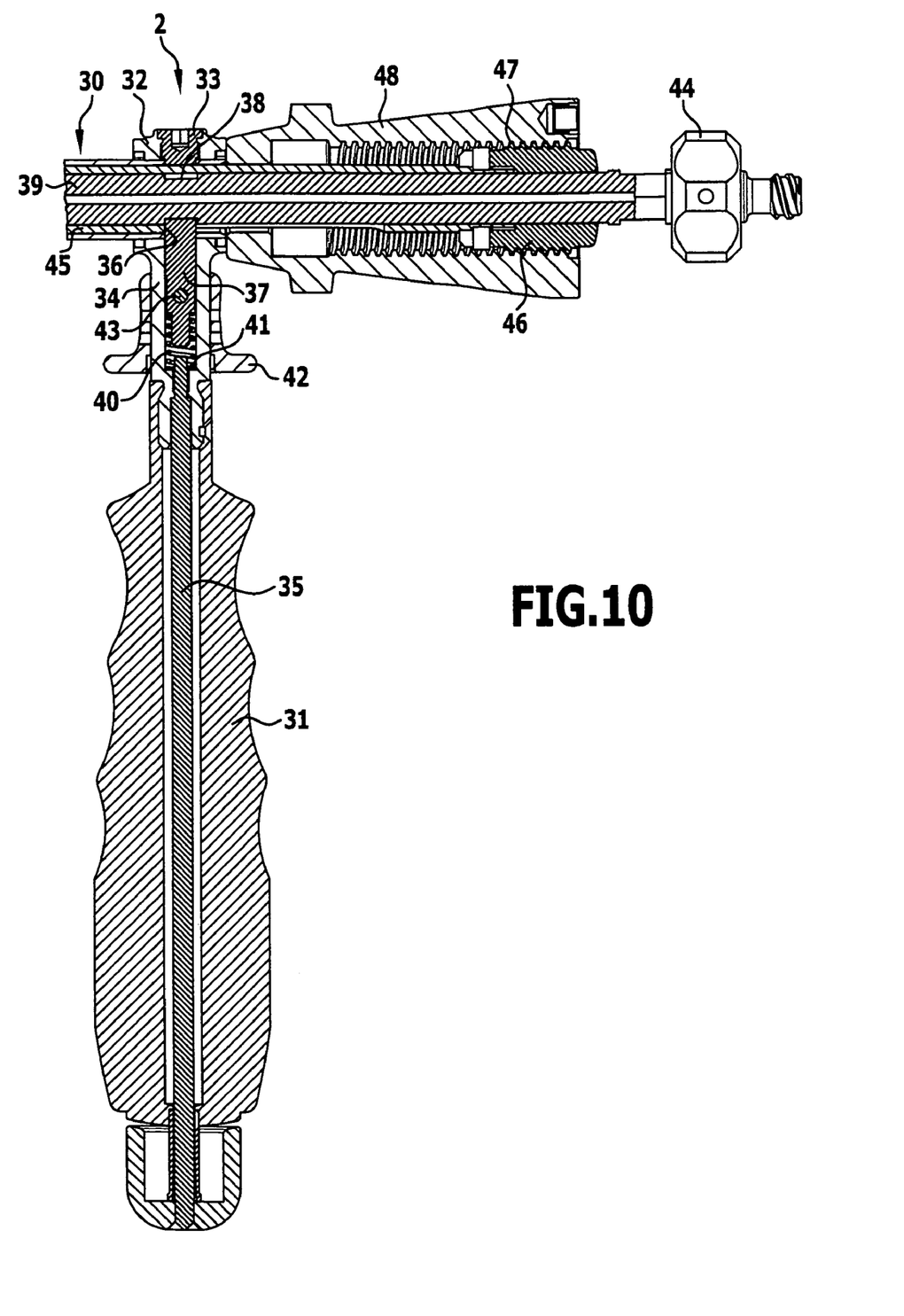

The arms 59 and 60 having the gripping projections 61 and 62 disposed on the distal end may be flexibly bent in a radial outward direction, thereby allowing the mutual spacing of the gripping projections 61 and 62 to be increased in such a way that the gripping projections 61 and 62 may slide past the clamping projections 65 and 66, in the manner shown in FIG. 7.

However, such a flexible bending-apart of the arms 59 and 60 is possible only if the shank 30 is retracted relative to the clamping sleeve to such an extent that the arms 59 and 60 are released by the shank 30. If, on the other hand, the shank 30 is advanced in distal direction relative to the clamping sleeve 45, the shank 30 overlaps the arms 59 and 60 and prevents them from bending flexibly apart, with the result that the spacing of the gripping projections 61 and 62 cannot be increased and the gripping projections 61 and 62 in this position are unable to slide past the clamping projections 65, 66, rather they position themselves laterally against the clamping projections 65 and 66 when the clamping sleeve 45 is drawn still further into the shank 30. This may be achieved by twisting the turning handle 48. During this proximal movement of the clamping sleeve 45, the gripping projections 61 and 62 position themselves against the clamping projections 65 and 66 and draw these and hence the entire implant in proximal direction, i.e. towards the shank 30. In this case, the projections 49 and 50 are supported against the side walls of the indentations 51 and 52. What therefore occurs is a clamping of the implant 1 to the shank 30, i.e. to the entire handling instrument 2. In the clamped state, the charging tube 39 engages in the region of the recess 54 over the head 17 of the attachment screw 16, simultaneously forming a rotational positive connection, the sealing aperture 56 moreover engaging over the charging connection piece 21, wherein a sealing effect is achieved in this region by means of the annular seal 58.

In this state, a hydraulic medium may be introduced via the charging tube 39 through a flow channel 22 into the interior 23 of the implant 1, the charging tube 39 therefore acting as a hydraulic pipe, so that the two locating parts 3 and 4 are pushed apart from one another. Once the desired spacing has been achieved in this way, simply by twisting the charging tube about the longitudinal axis the attachment screw 16 may be screwed in the internally threaded connection piece 14 and therefore press the clamping ring 27 towards the base 26 of the indentation 25, i.e. the two locating parts 3 and 4 are therefore fixed relative to one another in terms of their mutual spacing.

As soon as this has occurred, the interior 23 may be emptied. By means of the turning handle 48 the clamping sleeve 45 is then displaced relative to the shank once more in distal direction, so that finally a flexible outward swivelling of the arms 59 and 60 and the gripping projections 61 and 62 is possible, thereby allowing the handling instrument 2 to be removed from the implant 1. The two locating parts 3 and 4 of the handling instrument 2 then remain permanently with the adjusted spacing relative to one another.

As the handling instrument 2 accommodates all of the instrument parts needed to handle the implant 1 in the cross section of the shank 30, the access to the implant 1 for handling is possible through a very small body opening, and through this small opening it is possible to carry out both the connection to the implant and the filling of the implant 1 and hence both the adjustment of the spacing and the fixing of the two locating parts 3 and 4 relative to one another, and moreover subsequently the detachment of the handling instrument 2 from the implant 1.

The invention claimed is:

1. Vertebral body replacement implant, comprising:
    a bottom locating part for positioning against a lower vertebral body,
    a top locating part for positioning against an upper vertebral body, wherein the top and the bottom locating parts are telescopically displaceable relative to one another in a manner of a piston-cylinder unit,
    a sealed hydraulic chamber formed by the top and the bottom locating parts,
    a charging opening leading into the hydraulic chamber for a hydraulic medium, which upon entering the hydraulic chamber pushes the top and the bottom locating parts apart from one another, and
    a locking device, adapted to be activated by means of an instrument and upon activation fixes the top and the bottom locating parts non-displaceably relative to one another,
    wherein:
        the locking device is disposed on the vertebral body replacement implant in a region of the charging opening; and the charging opening and the locking device are disposed coaxially with one another.

2. Vertebral body replacement implant according to claim 1, wherein the locking device surrounds the charging opening.

3. Vertebral body replacement implant according to claim 1, wherein the charging opening is disposed in a charging connection piece and the locking device surrounds the charging connection piece.

4. Vertebral body replacement implant according to claim 1, wherein the locking device comprises a screw that is screwable into a thread of one of the top and the bottom locating parts and directly or by means of an intermediate element presses against the other of the top and the bottom locating parts and thereby fixes the top and the bottom locating parts relative to one another.

5. Vertebral body replacement implant according to claim 4, wherein the screw has a central through-channel that surrounds the charging connection piece.

6. Vertebral body replacement implant according to claim 4, wherein the intermediate element is a ring that surrounds the charging opening.

* * * * *